United States Patent [19]

Elsner et al.

[11] 4,351,960

[45] Sep. 28, 1982

[54] PRODUCTION OF AN ISOMERIC MIXTURE OF SECONDARY PHOSPHINES

[75] Inventors: Georg Elsner, Hürth; Hartfrid Vollmer; Gero Heymer, both of Erftstadt, all of Fed. Rep. of Germany

[73] Assignee: Hoechst Aktiengesellschaft, Fed. Rep. of Germany

[21] Appl. No.: 190,448

[22] Filed: Sep. 24, 1980

[30] Foreign Application Priority Data

Sep. 29, 1979 [DE] Fed. Rep. of Germany ....... 2939588

[51] Int. Cl.³ .............................................. C07F 9/50
[52] U.S. Cl. ....................................................... 568/8
[58] Field of Search ............................................ 568/8

[56] References Cited

U.S. PATENT DOCUMENTS 2,584,112 2/1952 Brown ..................................... 568/8
2,957,931 10/1960 Hamilton et al. ...................... 568/8

Primary Examiner—Helen M. S. Sneed
Attorney, Agent, or Firm—Connolly and Hutz

[57] ABSTRACT

The invention relates to a process for making an isomeric mixture of secondary phosphines with the summation formula $C_{20}H_{27}P$. To this end, hydrogen phosphide is reacted with dicyclopentadiene in the presence of an agent yielding free radicals. More specifically, hydrogen phosphide and dicyclopentadiene are used in a molar ratio of 1 to at least 2 and the reaction is effected under a pressure of 5 to 90 bars. The mixture is used in the production of flotation aids and as an ingredient of catalytically active transition metal complexes.

4 Claims, No Drawings

PRODUCTION OF AN ISOMERIC MIXTURE OF SECONDARY PHOSPHINES

The present invention relates to a process for making an isomeric mixture of secondary phosphines, and to the use of the mixtures so made.

U.S. Pat. No. 2,957,931 describes in general terms the preparation of organic phosphorus compounds. Typical of these compounds is the fact that at least one organic radical is connected to the phosphorus by means of a direct carbon/phosphorus-bond.

Compounds of this type are obtained by reacting phosphorus compounds which present at least one phosphorus/hydrogen-bond with organic compounds which present at least one carbon/carbon-double bond, the reaction being effected at temperatures within the range 20° to 300° C.

As disclosed in U.S. Pat. No. 2,957,931, compounds suitable for use in the above reaction inter alia include hydrogen phosphide ($PH_3$) and dicyclopentadiene (briefly termed DCP hereinafter). It has also been disclosed in this patent that agents yielding free radicals beneficially influence the reaction between the phosphorus and unsaturated organic compounds. This is also known from Journal of Organic Chemistry, vol. 26, (1961), pages 5138–45.

An adverse effect associated with the process described in U.S. Pat. No. 2,957,931 resides in the fact that the reaction produces minor yields only or, in the event of the olefin being used in excess, entails the formation of tertiary phosphines (cf. examples 68 and 69).

The present invention now unexpectedly provides a process for making an isomeric mixture of secondary phosphines from $PH_3$ and DCP, which comprises reacting $PH_3$ and DCP in a molar ratio of 1 to at least 2 under a pressure of 5 to 90 bars, preferably 15 to 30 bars, the isomeric mixture being obtained practically in quantitative yield.

It has been found that by the use of stoichiometric quantities, i.e. by the use of $PH_3$ and DCP in the molar ratio of 1:2, it is possible to obtain secondary phosphines quantitatively. These compounds have a very pronounced tendency to form; even in the presence of a large excess of hydrogen phosphide ($PH_3$:DCP=5:1) considerable proportions of secondary phosphines are always obtained (together with primary phosphines).

No tertiary phosphine is, however, obtained upon the use of the olefin in excess. A further unexpected result is the short reaction time of about 2 hours for an about 190 molar batch.

It is preferable, however, to react $PH_3$ and DCP in a molar ratio of 1:2, the resulting reaction product being distilled, if desired, and the fraction distilling over at 155° to 157° C. under 0.05 millibar being collected.

In view of a preconception long held in the art that the formation of primary phosphines tends to be favored by increasing pressure, the artisan would not have expected secondary phosphines to be formed preferentially.

The reaction of DCP with $PH_3$ entails the formation of a plurality of isomers. The exact constitution of the reaction product has not yet been defined.

Agents yielding free radicals which find use in the present process include those which are known to catalyze the reaction of $PH_3$ with olefins, and which have been specified in the above references.

Use can more particularly be made of azo-bis-isobutyronitrile (briefly termed ABIN hereinafter), or di-t-butyl peroxide, which should preferably be used in the form of a solution in an inert organic solvent.

The isomeric mixture of novel secondary phosphines is suitable, for example, for use as an intermediary product in the production of flotation aids or as a modifying ingredient of catalytically active transition metal complexes.

The following Examples illustrate the invention:

EXAMPLE 1

30 kg DCP was placed in an 80 liter autoclave provided with a stirrer, various tubular inlets and a double jacket. Next, the material was cooled down to −10° C., the autoclave was evacuated and 2.57 kg $PH_3$ was condensed thereinto so as to establish a molar ratio of DCP:$PH_3$ of 3:1. The mixture was heated to 90° C. Next, 3 l of a saturated solution of ABIN in toluene was pumped into the apparatus within 2 hours by means of a dosing pump. After that time, the strongly exothermal reaction was complete. A specimen was taken and analyzed by $^{31}P$-NMR-spectroscopy. A broad signal which had multiplett structure was found at +34 ppm. Judging from its position, it originated from a mixture of secondary phosphines. Primary or tertiary phosphine could not be found to have been formed. Toluene and DCP were distilled off and a viscous yellowish oil which contained 10.1 weight % phosphorus (10.4 weight %, based on secondary phosphine) was obtained. The reaction was effected under a pressure of 17.5 bars which dopped down to about 5 bars towards the end of the reaction.

EXAMPLE 2

The procedure was as in Example 1. 40 kg DCP was reacted with 5.3 kg $PH_3$. This corresponded to the use of DCP and $PH_3$ in a molar ratio of about 2:1. The reaction was terminated after 2 hours. Low boiling matter was removed and a very viscous yellowish oil which contained 10.3 weight % phosphorus was obtained in almost quantitative yield. The reaction was effected under a pressure of 22 bars which dopped down to about 3 bars at the end of the reaction.

We claim:

1. In the process for making secondary phosphines by reacting under reaction conditions of pressure hydrogenphosphide with dicyclopentadiene in the presence of a catalyst, the improvement which comprises: reacting the hydrogen phosphide with the dicyclopentadiene in a molar ratio of 1:at least 2 and in the presence of azo-bis-isobutyronitrile or di-t-butylperoxide as catalyst, with the resulting formation of a mixture consisting essentially of isomeric secondary phosphines having the summation formula $C_{20}H_{27}P$.

2. The process as claimed in claim 1, wherein hydrogen phosphide and dicyclopentadiene are reacted in a molar ratio of 1:2.

3. The process as claimed in claim 1, wherein the reaction is effected under a pressure of 15 to 30 bars.

4. The process as claimed in claimed 1, wherein the reaction product is distilled and the fraction distilling over at 155° to 157° C. under a pressure of 0.05 millibar is collected.

* * * * *